United States Patent [19]

Yabe et al.

[11] Patent Number: 5,297,620

[45] Date of Patent: Mar. 29, 1994

[54] METHOD AND APPARATUS FOR TRANSPORTING, UTILIZING AND RECOVERING HEAT UTILIZING DECOMPOSING AND SYNTHESIZING REACTIONS OF METHANOL

[75] Inventors: Akira Yabe; Iwao Yamashita; Naoki Endo, all of Tsukuba, Japan

[73] Assignee: Agency of Industrial Science & Technology, Ministry of International Trade & Industry, Tokyo, Japan

[21] Appl. No.: 38,868

[22] Filed: Mar. 29, 1993

[30] Foreign Application Priority Data

Mar. 31, 1992 [JP] Japan .................................. 4-105489

[51] Int. Cl.$^5$ ........................... F24J 1/00; F28D 21/00
[52] U.S. Cl. ............................. 165/104.12; 126/263 R; 431/2
[58] Field of Search ................... 165/104.12; 126/263; 431/2

[56] References Cited

FOREIGN PATENT DOCUMENTS 2457391 10/1976 Fed. Rep. of Germany ........................ 165/104.12

Primary Examiner—Albert W. Davis, Jr.
Attorney, Agent, or Firm—Oblon, Spivak, McClelland, Maier & Neustadt

[57] ABSTRACT

A method for transportation, utilization and recovery of heat comprises the wide-area installation of methanol and reformed gas supply pipelines, combustion of the methanol and reformed gas to obtain high-temperature heat, subjecting reformed gas supplied from the reformed gas supply pipeline to an exothermic reform reaction and feeding the methanol thus produced into the methanol supply pipeline to obtain low-temperature heat, subjecting methanol supplied from the methanol supply pipeline to an endothermic reform reaction and feeding the reformed gas thus produced into the reformed gas supply pipeline and recovering the waste heat that is generated.

9 Claims, 2 Drawing Sheets

METHOD AND APPARATUS FOR TRANSPORTING, UTILIZING AND RECOVERING HEAT UTILIZING DECOMPOSING AND SYNTHESIZING REACTIONS OF METHANOL

BACKGROUND OF THE INVENTION

1. Field of the Invention

This invention relates to a method and apparatus for efficiently utilizing and recovering heat utilizing a decomposing reaction of methanol that generates reformed gas (hereinafter referred to as "endothermic reform reaction") and synthesizing reaction of reformed gas to produce methanol (hereinafter referred to as "exothermic reform reaction") for simplifying the transportation of recovered heat together with a simple wide area transport of heat in the form of methanol and reformed gas by providing pipelines that extend over a wide area for the delivery of methanol and reformed gas.

2. Description of the Prior Art

Previously heat recovery, utilization and transportation, have been limited to relatively localized areas and such transportation, utilization and recovery operations have been implemented separately. Moreover, recovered waste heat and recovered heat discharged at designated locations is reutilized at the same place that the heat was first utilized and recovered. It is extremely difficult to transport such heat to remote areas for utilization, and the heat efficiency is poor. In addition, owing to the difficulty of ensuring the economic efficiency, heat transportation and utilization using piped hot-water and steam has been limited to a distance of some several kilometers, and over greater distances has been virtually non-existent.

A method is known in which a carbon oxide based endothermic reform reaction is utilized to supply a fuel cell with hydrogen produced from methane. This method uses a relatively high temperature (300 to 800 degrees) heat source. Also known are heat recovery systems in which heat discharged by a combustion means is used to preheat the air used in the combustion process or for heating a fluid. Also known are systems which apply waste heat energy to effect the transfer of fluids or gases, or in which the waste heat medium itself is transferred for recovery and reutilization.

Moreover, from the viewpoint of heat utilization efficiency and heat utilization format, in using waste heat utilization and recovery it is desirable that the original exergy (concerning which, see below) be improved, but in the case of conventional heat utilization methods and systems this has not been done and, therefore, efficient utilization has not been possible.

The concept of exergy will now be explained. From the viewpoint of the quality of heat energy utilization, it is not enough to discuss just the total amount of energy; instead, it must be discussed in terms of the amount of energy that can be converted into work (which energy shall hereinafter be referred to as "exergy") or "available energy."

Here, exergy A signifies the maximum amount of work that can be obtained from that energy, which in a fluid system can be defined by the following equation.

$$A = H - H_o - T_o(S - S_o)$$

Here, H is enthalpy, S is entropy and T is absolute temperature, and the subscripted characters indicate the state of the surrounding environment.

The energy Q possessed by this fluid system state is $$Q = H - H_o.$$

Based on the law of the conservation of energy in accordance with which heat exchange or heat conversion does not change the total amount of energy, a discharge of energy by a system results in a loss of enthalpy and energy, but the energy of the receiving side increases by the amount of energy received. However, the reduction in exergy A brought about by this transfer of energy will always be larger than the amount of increase in the exergy of the receiving side. That is, while the total amount of energy Q is always conserved, the total amount of exergy A will continue to decrease with the transfer of the energy.

Here we shall consider the proportion of the total amount of energy that can be converted into exergy. As the exergy will continue to decline while the total amount of energy remains constant, we can say that the ratio of exergy to the energy possessed by a substance represents the quality of the energy of that substance. We shall call the value that represents this energy quality the exergy ratio $\dot{\eta}$. That is, if P is pressure, in a gas where $T > T_o$ and $P = P_o$, the exergy ratio $\dot{\eta}$ is obtained by the following equation.

$$\dot{\eta} = 1 - T_o(S - S_o)/(H - H_o).$$

Generally when we consume energy, more accurately it means that we are consuming exergy, and the exergy ratio $\dot{\eta}$ decreases with each consumption. Considered from the viewpoint of this exergy, fossil fuel can be termed a higher-quality (higher exergy ratio) fuel than hydrogen, while considered from the viewpoint of this exergy, waste heat is a lower-quality (lower exergy ratio) energy than hydrogen.

In recovering and reutilizing waste heat energy, it is preferable to raise the exergy ratio for recovery purposed. In order to accomplish this it is necessary to supply from somewhere an amount of exergy that is more than the amount by which the exergy needs to be increased.

With the decomposition by endothermic reaction of a hydrocarbon into hydrogen and carbon monoxide or carbon dioxide means that hydrogen, a low exergy ratio fuel, is generated from hydrocarbon, a fuel having a high exergy ratio, which from the viewpoint of the effective utilization of heat energy is not desirable. On the other hand, however, the carbon dioxide generated by the reform reaction can be easily recovered without being released into the atmosphere and, moreover, the generation of hydrogen, a clean fuel, means that a fuel is thus obtained that is effective in environmental terms. And, if waste heat is used to obtain the necessary heat for the endothermic reform reaction, it means that waste heat having a low exergy ratio can be raised to the higher exergy ratio of hydrogen.

As mentioned, previously methods and systems for the recovery, utilization and transportation of thermal energy have been limited to relatively localized areas and such transportation, utilization and recovery operations have been implemented separately. Also, transporting such heat a substantial distance, such as several tens of kilometers, has been difficult and the loss so great that it has not been practiced to any real extent.

Also, in the case of the conventional method that utilizes a carbon oxide based endothermic reform reaction, the heat source used in the reaction is a relatively high temperature one (300 to 800 degrees). To apply waste heat for this reaction would therefore mean having to use waste heat at such a high temperature that, in practical terms, it would be difficult to utilize waste heat produced by a factory or generated in the region.

In general systems that utilize waste heat energy only use it to preheat air used in a combustion process, or to heat a fluid, and are not set up to raise the exergy ratio of waste heat for recovery and reutilization. Also, when waste heat energy is used to be transferred to another place for utilization, this can only be done by shifting the energy into a gas or fluid which is then moved, or by moving the waste heat medium itself, a procedure which inevitably is accompanied by a large loss of the energy from thermal radiation.

OBJECT AND SUMMARY OF THE INVENTION

An object of the present invention is to provide a method and apparatus for wide-area transportation, utilization and recovery of heat utilizing decomposing and synthesizing reactions of methanol whereby the wide-area transportation, utilization and recovery of heat can be accomplished efficiently and the heat energy of low-exergy-ratio waste heat is formed into an energy medium (fuel) having a higher exergy ratio for recovery and, moreover, transportation of the recovered energy medium can be readily accomplished, and as during such transportation there is no loss of energy the medium used to transport the heat can also be utilized as fuel as it is.

For attaining this object, the present invention provides a method for the transportation, utilization and recovery of heat utilizing decomposing and synthesizing reactions of methanol, comprising providing a methanol supply pipeline extending over a wide area together with a supply pipeline arrangement for supplying a reformed gas that is a mixture of hydrogen and carbon monoxide or carbon dioxide, obtaining high-temperature heat by direct combustion of the methanol and reformed gas, subjecting reformed gas supplied from the reformed gas supply pipeline to an exothermic reform reaction ($CO+2H_2 \rightarrow CH_3OH$, or $CO_2+3H_2 \rightarrow CH_3OH+H_2O$) and feeding the methanol thus produced into the methanol supply pipeline to obtain low-temperature heat, subjecting methanol supplied from the methanol supply pipeline to an endothermic reform reaction ($CH_3OH \rightarrow CO+2H_2$ or $CH_3OH+H_2O \rightarrow CO_2+3H_2$) and feeding the reformed gas thus produced into the reformed gas supply pipeline and recovering the waste heat that is generated.

The above object is also attained by an apparatus for transporting, utilizing and recovering heat by utilizing decomposing and synthesizing reactions of methanol, said apparatus comprising a high-temperature heat utilization unit, a low-temperature heat utilization unit, and a heat recovery unit, a supply pipeline for supplying methanol to the above three units, and a supply pipeline for supplying the above three units with reformed gas that is a mixture of hydrogen and carbon monoxide or carbon dioxide, wherein the high-temperature heat utilization unit includes a combustion means in which methanol and reformed gas supplied by the supply pipelines are subjected to direct combustion, the low-temperature heat utilization unit is provided with a low-temperature heat generator that includes a reaction chamber to which reformed gas is input from the reformed gas supply pipeline and which carries out an exothermic reform reaction to produce methanol ($CO+2H_2 \rightarrow CH_3OH$, and $CO_2+3H_2 \rightarrow CH_3OH+H_2O$) and feeds the methanol thus produced to the methanol supply pipeline, and the heat recovery unit includes a heat recovery device to which methanol is input from the methanol supply pipeline and which carries out an endothermic reform reaction ($CH_3OH \rightarrow CO+2H_2$ or $CH_3OH+H_2O \rightarrow CO_2+3H_2$) and feeds the reformed gas thus produced to the reformed gas supply pipeline and is provided with a heat exchanger that applies to the heat recovery device waste heat generated in the region.

Thus, in accordance with the present invention, methanol and reformed gas supply pipelines are installed over a wide area and a high-temperature heat utilization unit is used for combustion of reformed gas and methanol to obtain the necessary heat, and the exhaust gases are fed to an adjoining heat recovery unit. A low-temperature heat utilization unit is used for combustion of reformed gas to obtain heat of around 150° C. to 250° C. and feed the methanol that produced to the methanol supply pipeline. The heat recovery unit uses waste heat from the high-temperature heat utilization unit or the waste heat from an adjoining garbage incinerator to produce reformed gas from methanol and feed the reformed gas to the reformed gas supply pipeline.

In this way, waste heat is utilized to convert methanol to high-exergy reformed gas for recovery and transportation, whereby the recovered heat can be readily supplied to a remote location without incurring a large loss of heat. Moreover, as methanol is used as the reaction medium, reaction is implemented at a relatively low temperature.

The above and other features of the present invention will become apparent from the following description made with reference to the drawings.

DETAILED DESCRIPTION OF THE PREFERRED EMBODIMENTS

An embodiment of the present invention will now be described with reference to the drawings.

Figure 1:
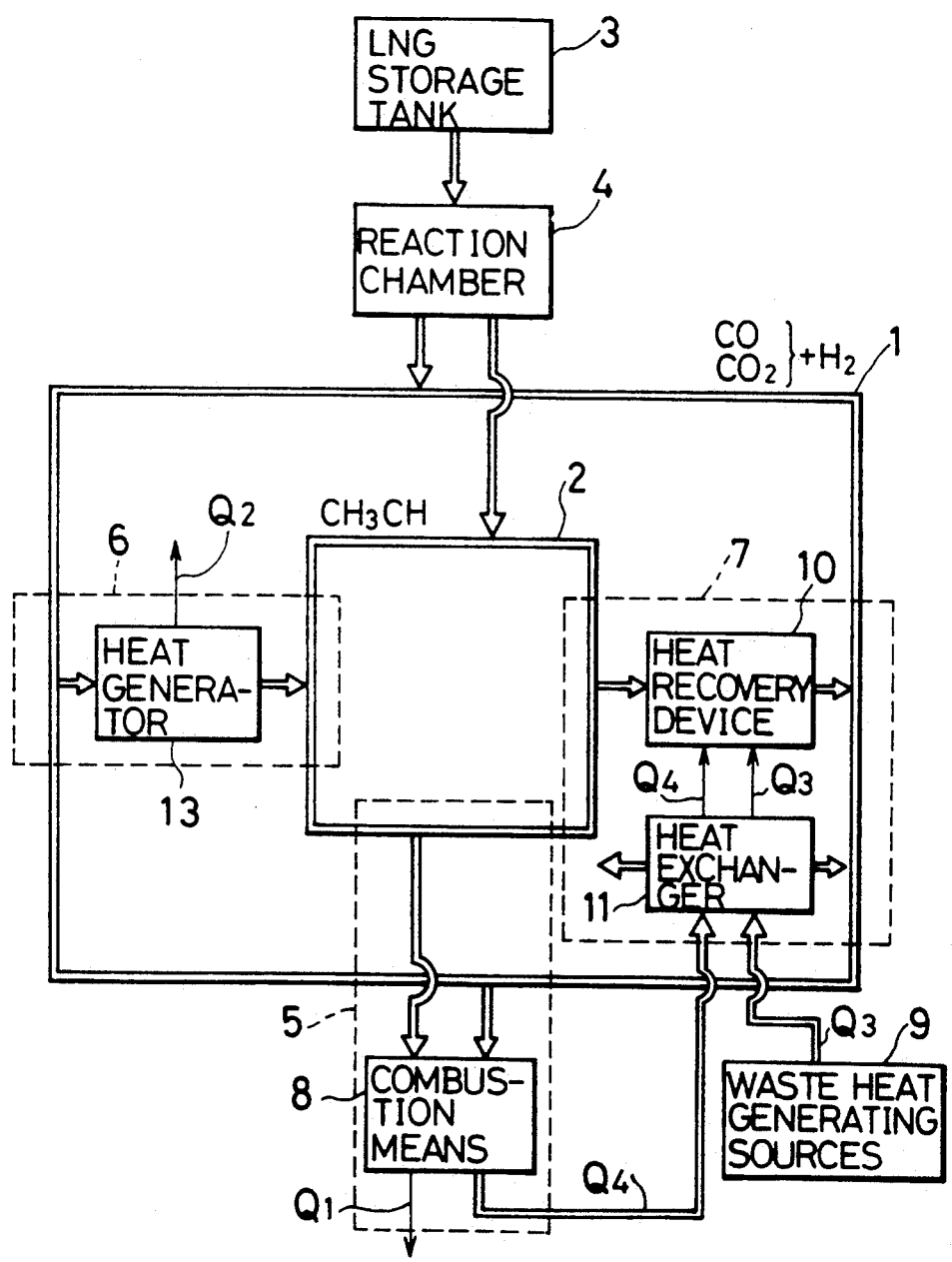
FIG. 1 is a schematic diagram illustrating heat transportation, utilization and recovery according to the present invention.

FIG. 1 is a schematic diagram of a heat transportation, utilization and recovery system according to an embodiment of the present invention. With reference to the drawing, a pair of pipelines 1 and 2 are laid side by side over a wide area. The pipelines are, for example, from several kilometers to several tens of kilometers in length.

A reaction chamber 4 is connected with a Liquified natural gas (LNG) storage tank 3. LNG supplied from the storage tank 3 is reformed in the reaction chamber 4 to produce a mixture of carbon monoxide (CO) or carbon dioxide ($CO_2$) (hereinafter referred to as "carbon oxide") and hydrogen ($H_2$) (which mixture shall hereinafter be referred to as "reformed gas"), and methanol ($CH_3OH$). The reformed gas produced in the reaction chamber 4 is fed into the reformed gas pipeline and the methanol into the methanol pipeline 2 for wide-area distribution.

Located within the wide area covered by the pipelines 1 and 2 are numerous factories, households and public facilities. In such facilities are high-temperature heat utilization units 5 that require high-temperature heat, low-temperature heat utilization units 6 that require relatively low-temperature heat, and heat recovery units 7 which recover heat discharged from such facilities in the form of waste gas or water, each being connected to the pipelines 1 and 2.

The high-temperature heat utilization units 5 may be factory boiler burners or furnaces, and are arranged so that reformed gas in the pipeline 1 is delivered to a combustion means 8 for direct combustion, and methanol in pipeline 2 is subjected to direct combustion, to obtain heat $Q_1$.

The combustion of reformed gas by a high-temperature heat utilization unit 5 is represented by the following reaction formula.

$$CO + 3H_2 2O_2 \rightarrow CO_2 3H_2O + \text{Heat value (1008 kJ/mol)}.$$

Similarly, the combustion of methanol by a high-temperature heat utilization unit 5 is represented by the following reaction formula.

$$CH_3OH + 3/2O_2 \rightarrow CO_2 + 2H_2O + \text{Heat value (676 kJ/mol)}.$$

Figure 3:
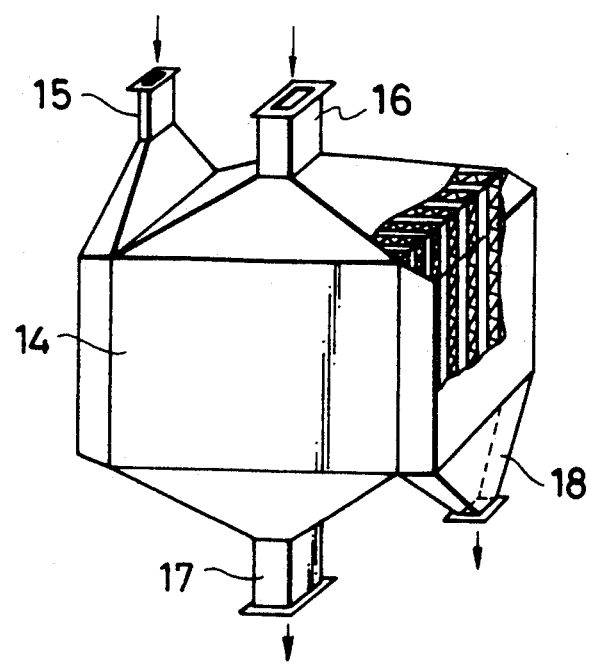
FIG. 3 is a perspective view of a heat generating means that can be used in the present invention.

The low-temperature heat utilization units 6 require relatively low-temperature heat in the order of 150 to 250 degrees celsius for regional heating and cooling, hot water delivery and the like. A heat generator 13 is used to subject reformed gas in the pipeline 1 to an exothermic reform reaction to thereby synthesize methanol and obtain relatively low-temperature heat $Q_2$. The synthesized methanol is supplied to pipeline 2. An example of such a heat generator is shown in FIG. 3. As shown by FIG. 3, on the upstream side of a reaction chamber main unit 14 are an inlet 15 via which a heated fluid such as water or steam is supplied, and an inlet 16 via which reformed gas is supplied, while on the downstream side are a methanol discharge outlet 17 and a heated fluid takeoff outlet 18. The main unit 14 is charged with a catalyst for synthesizing methanol. Reformed gas is brought in via the inlet 16, converted in the presence of the catalyst, a noble metal such as Pt or Ru, and discharged. The heated fluid is similarly discharged.

The following reactions take place in the above heat generator.

$$CO + 2H_2 \rightarrow CH_3OH + \text{Heat value (91 kJ/mol)}$$

$$CO_2 + 3H_2 \rightarrow CH_3OH + H_2O + \text{Heat value (131 kJ/mol)}.$$

The heat recovery units 7 recover waste heat $Q_3$ from waste heat generating sources 9 such as factories and garbage incineration centers, or recovers the heat $Q_4$ of the exhaust from the combustion means 8 of the high-temperature heat utilization units 5, and has a heat recovery device 10 that subjects methanol in the pipeline 2 to an endothermic reform reaction to thereby decompose the methanol to reformed gas. Waste heats $Q_3$ and $Q_4$ are supplied to the heat recovery device 10 via a heat exchanger 11. The result is that the methanol is decomposed to carbon oxide which is delivered to the pipeline 1. In this way, by converting methanol to reformed gas the exergy is raised for the heat recovery. The structure of the heat exchanger 11 does not have to be one that is generally employed for such devices, but includes an arrangement whereby the waste heat is applied directly to the heat recovery device 10.

An example of such a heat recovery device will now be described with reference to FIG. 3. On the upstream side of a main unit 14 is a waste heat inlet 15, and on the downstream side is an outlet 18. A methanol inlet 16 is provided on the top part of the main unit 14 and a reformed gas discharge outlet 17 is provided on the bottom part. The main unit 14 is charged with a methanol-decomposing catalyst that heated by waste heat supplied via the inlet 15, methanol introduced via the inlet 16 is contacted with the catalyst, a noble metal such as Pt or Ru, giving rise to an endothermic reaction whereby the methanol is decomposed into carbon gas and hydrogen, and discharged via the outlet 17.

The following are the endothermic reform reactions that take place in the heat recovery device, at a relatively low temperature (250 to 150 degrees celsius).

$$CH_3OH \rightarrow CO + 2H_2 + \text{Heat value (91 kJ/mol)}$$

$$CH_3OH + H_2O \rightarrow CO_2 + 3H_2 + \text{Heat value (131 kJ/mol)}.$$

Although the illustrated heat recovery unit 7 was shown as using the exhaust heat of a high-temperature heat utilization unit 5 in a different, remote location, this was just an example representation made for the purpose of explaining the functions of the high-temperature heat utilization unit 5; the exhaust heat of a high-temperature heat utilization unit 5 is supplied to an adjacent heat recovery unit 7.

Figure 2:
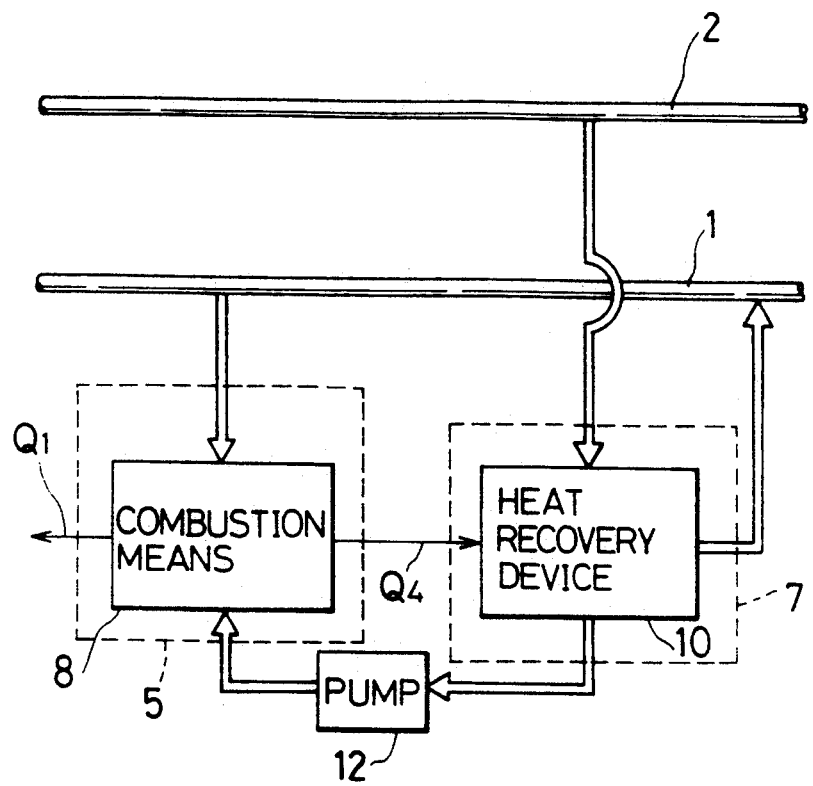
FIG. 2 is a schematic diagram illustrating the way the high-temperature heat utilization unit and heat recovery unit are connected according to another embodiment.

FIG. 2 shows another embodiment of a high-temperature heat utilization unit according to the present invention. In this embodiment the combustion means 8 of a high-temperature heat utilization unit 5 is located adjacent to the heat recovery device 10 of a heat recovery unit 7, with the combustion means 8 utilizing heat $Q_1$ generated by the combustion of reformed gas delivered from the pipeline 1 and sending waste gas heat $Q_4$ to the heat recovery device 10. The heat recovery device 10 uses this heat $Q_4$ to reform methanol from the pipeline 2 to produce reformed gas, which is circulated to the combustion means 8 and the pipeline 1 by a pump 12.

It is to be understood that the present invention is not limited to the embodiment system described above. For example, as it is possible to recover the carbon dioxide itself that is contained in the reformed gas, using an arrangement whereby the carbon dioxide in the reformed gas is recovered and just the hydrogen is burned would provide combustion that is clean, with none of the environmental pollution caused by combustion using carbon dioxide. Moreover, the exhaust heat of the high-temperature heat utilization unit can be utilized by a means other than a heat recovery means.

Thus, as described in the foregoing, in accordance with the present invention the transportation, utilization and recovery of heat can be accomplished over a wide area simply by providing a double pipeline. And as waste heat can be recovered in reformed gas, the recovered heat can be readily transported to a remote location with no heat loss, thereby making it possible for waste heat to be exchanged between wide areas.

In addition, the fact that, compared to the hydrocarbon endothermic reform reaction of the prior art the heat used in the endothermic reform reaction of this invention is at a relatively low temperature (around 150° C. to 250° C.), the efficiency of the waste heat is improved. Also, as waste heat is converted to reformed gas for recovery the recovery takes place in a high exergy format, whereby the recovery efficiency is improved and there is no problem about the utilization format of the thermal energy following recovery.

What is claimed is:

1. A method for transporting, utilizing and recovering heat utilizing decomposing and synthesizing reactions of methanol, comprising:

arranging a methanol supply pipeline and a pipeline for supplying a reformed gas mixture of hydrogen and carbon oxide, obtaining high-temperature heat by direct combustion of methanol and reformed gas supplied by said pipelines, subjecting reformed gas supplied from the reformed gas supply pipeline to an exothermic reform reaction to obtain low-temperature heat and transferring the methanol thus produced to the methanol supply pipeline, and utilizing waste heat to subject methanol supplied from the methanol supply pipeline to an endothermic reform reaction and feeding reformed gas thus produced into the reformed gas supply pipeline and recovering the waste heat.

2. A method according to claim 1 in which low-temperature heat in the order of 150° C. to 250° C. obtained from said reformed gas exothermic reform reaction is used for regional heating and cooling and supplying hot water.

3. A method according to claim 1 in which regional waste heat in the order of 150° C. to 250° C. is used in said methanol endothermic reform reaction.

4. A method according to claim 1 in which said methanol endothermic reform reaction uses heat of waste gas generated by direct combustion of methanol.

5. An apparatus for transporting, utilizing and recovering heat by utilizing decomposing and synthesizing reactions of methanol, said apparatus comprising:

high-temperature heat utilization means, low-temperature heat utilization means, heat recovery means, means for supplying waste heat to the heat recovery means, a supply pipeline for supplying methanol to said three utilization and recovery means, and a supply pipeline for supplying said three utilization and recovery means with reformed gas mixture of hydrogen and carbon oxide, wherein the high-temperature heat utilization means includes combustion means in which methanol and reformed gas supplied by the supply pipelines are subjected to direct combustion, the low-temperature heat utilization means is provided with a low-temperature heat generation means which subjects reformed gas input from the reformed gas supply pipeline to an exothermic reform reaction and feeds methanol thus produced to the methanol supply pipeline, and the heat recovery means includes a heat recovery device which subjects methanol input from the methanol supply pipeline to an endothermic reform reaction and feeds reformed gas thus produced to the reformed gas supply pipeline.

6. An apparatus according to claim 5 that further comprises a heat exchanger via which waste heat from the waste heat supply means is supplied to the heat recovery means.

7. An apparatus according to claim 5 in which means for carrying out reformed gas exothermic reform reaction in the low-temperature heat utilization means obtains low-temperature heat in the order of 150° C. to 250° C. and supplies this heat to heating and cooling means and water heating means.

8. An apparatus according to claim 5 in which the high-temperature heat utilization means includes a heat recovery device that uses the heat of exhaust gas from the combustion means to reform methanol supplied from the methanol supply pipeline, and pump means for delivering reformed gas produced by the heat recovery device to the combustion means.

9. An apparatus for transporting, utilizing and recovering heat by utilizing decomposing and synthesizing reactions of methanol, said apparatus comprising:

high-temperature heat utilization means, low-temperature heat utilization means, and heat recovery means, a supply pipeline for supplying methanol to said three means, and a supply pipeline for supplying said three means with reformed gas mixture of hydrogen and carbon oxide, wherein the high-temperature heat utilization means includes combustion means for direct combustion of reformed gas from the reformed gas supply pipeline, a heat recovery device that uses the heat of exhaust gas from the combustion means to reform methanol supplied from the methanol supply pipeline and thereby produce reformed gas, and pump means for delivering reformed gas produced by the heat recovery device to the combustion means, the low-temperature heat utilization means includes a low-temperature heat generation means which subjects reformed gas input from the reformed gas supply pipeline to an exothermic reform reaction and feeds methanol thus produced to the methanol supply pipeline, and the heat recovery means includes a heat recovery device which subjects methanol input from the methanol supply pipeline to an endothermic reform reaction and feeds reformed gas thus produced to the reformed gas supply pipeline, wherein the heat recovery device includes a heat exchanger that provides the heat recovery device with regionally generated waste heat.

* * * * *